US00PP07959P

United States Patent [19]

Hanes

[11] Patent Number: Plant 7,959

[45] Date of Patent: Sep. 1, 1992

[54] GERANIUM NAMED ECLIPSE RED

[75] Inventor: Mitchell Hanes, Morgan Hill, Calif.

[73] Assignee: Goldsmith Seeds, Inc., Gilroy, Calif.

[21] Appl. No.: 666,886

[22] Filed: Mar. 8, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

[57] ABSTRACT

A new Geranium cultivar distinguished by its red semi-double flowers, and its dark green foliage; the plant being fast-rooting and having an open vigorous growth habit.

1 Drawing Sheet

BACKGROUND OF THE PLANT

The present invention comprises a new and distinct cultivar of Geranium, botanically known as *Pelargonium hortorum* Bailey, and hereinafter referred to by the cultivar name Eclipse Red. The new cultivar is a hybrid seedling resulting from a controlled crossing of a red single flower seed parent known as 590-1 and a scarlet colored semi-double flower pollen parent known as 196-5; both parents having been selected by me from my collection of plants maintained for breeding purposes at Gilroy, Calif.

This new Geranium cultivar is a product of a planned breeding program intended to create new Geranium cultivars with red colored flowers, semi-double flower form, dark green foliage, vigorous growth and superior cutting productivity.

The new cultivar was created in 1989 in the company nursery at Gilroy, Calif. and has been repeatedly asexually reproduced by cuttings in Gilroy, Calif. and in Guatemala over a 16 month period. It has also been trialed at Okemos, Mich. and in each case it has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of Eclipse Red. The data which defines these characteristics were collected from asexual reproductions carried out in Gilroy, Calif. The plant history was taken on 20 week old plants, blossomed under natural light in a greenhouse and color readings were taken in the greenhouse (in Gilroy, Calif.) on May 29, 1990 at 2 P.M. under ambient light. Color references are primarily to The R.H.S. Colour Chart of The Royal Horticultural Society of London, England (R.H.S.).

THE PLANT

Classification:

*Botanical.*—*Pelargonium hortorum* Bailey.

*Commercial.*—Zonal Geranium.

Form: Upright.

Height: 17 to 20 cm., as a 5½ inch potted plant, excluding blooms.

Growth: Fast-rooting and vigorous, upright open habit.

Strength: Strong grower for a dark leaf variety. Produces numerous flowers. Good shipping ability as rooted or unrooted cuttings.

Foliage: Abundant quantity.

Leaves:

*Size.*—Diameter about 3.5–5.0 cm.

*Shape.*—Rounded cordate with occasional upfolding between veins.

*Margin.*—Irregularly crenate.

*Texture.*—Leathery and pubscent on both surfaces, especially along veins.

*Ribs and veins.*—Distinctly palmate, 3.0 to 5.0 cm. long.

*Color.*—Upper side: Dark green with a light zone. Underside: Lighter green color without a zone. Ribs and veins not prominently different from upper surface.

*Petioles.*—About 5.0 to 8.0 cm. in length.

THE BUD

Size:

*Diameter.*—About 4 mm.

*Length.*—About 1.7 cm. at time of bud opening.

Shape: Pointed ovoid.

Color:

*When sepals first divide.*—RHS 53-B.

Sepals: Five in number, flat behind petals. Pointed linear lanceolate.

*Color in an open flower.*—Green RHS 137-C at tips with a purple-red base and pedicle RHS 59-A.

THE FLOWER

Blooming habit: Continuous throughout the year.

Size: Approximately 4.5–5.0 cm. diameter, 1.0 cm. deep, irregularly radially symmetrical.

Form: Cup-shaped when bloom first opens, later flattening to shallow cup shape with maturity.

Petals: Five imbricate outer petals, 2.2–2.4 cm. wide and approximately 2.0 cm. long. 3 to 6 inner smaller petaloids of varying shape. Both the outer petals and inner petaloids are red RHS 44-B. Color changing little with age. Underside of petals lighter. Petals and petaloids soft and satiny.

Pedicel: Approximately 2.5–3.0 cm. in length.

Persistence: Nonshattering flower.

INFLORESCENSE

Type: An umbel composed of approximately 26–31 flowers, erect or laterally ascending.

Peduncle: Approximately 11–15 cm. in length. Color ranging from green to red-purple.

REPRODUCTIVE ORGANS

Stamens:

*Anthers.*—Seven to nine 9 positioned below the mature stigma, dull red prior to anthesis.

*Pollen.*—Orange in color.

Pistil:

*Number.*—One.

*Length.*—Approximately 8 mm.

*Style.*—Length: About 3 mm. Color: Purplish red.

*Stigma.*—Five linear lobes of near equal length, curling back toward ovary, purplish-red.

*Ovaries.*—At anthesis, densely pubscent with white hairs, oblong. Green drying to a light brown at maturity.

Fruit: Partially fertile.

I claim:

1. A new and distinct cultivar of Geranium plant substantially as herein shown and described characterized by dark green foliage with zonation, red-colored, semi-double flowers on large umbels, the plant being fast-rooting and growing with an open, vigorous habit.

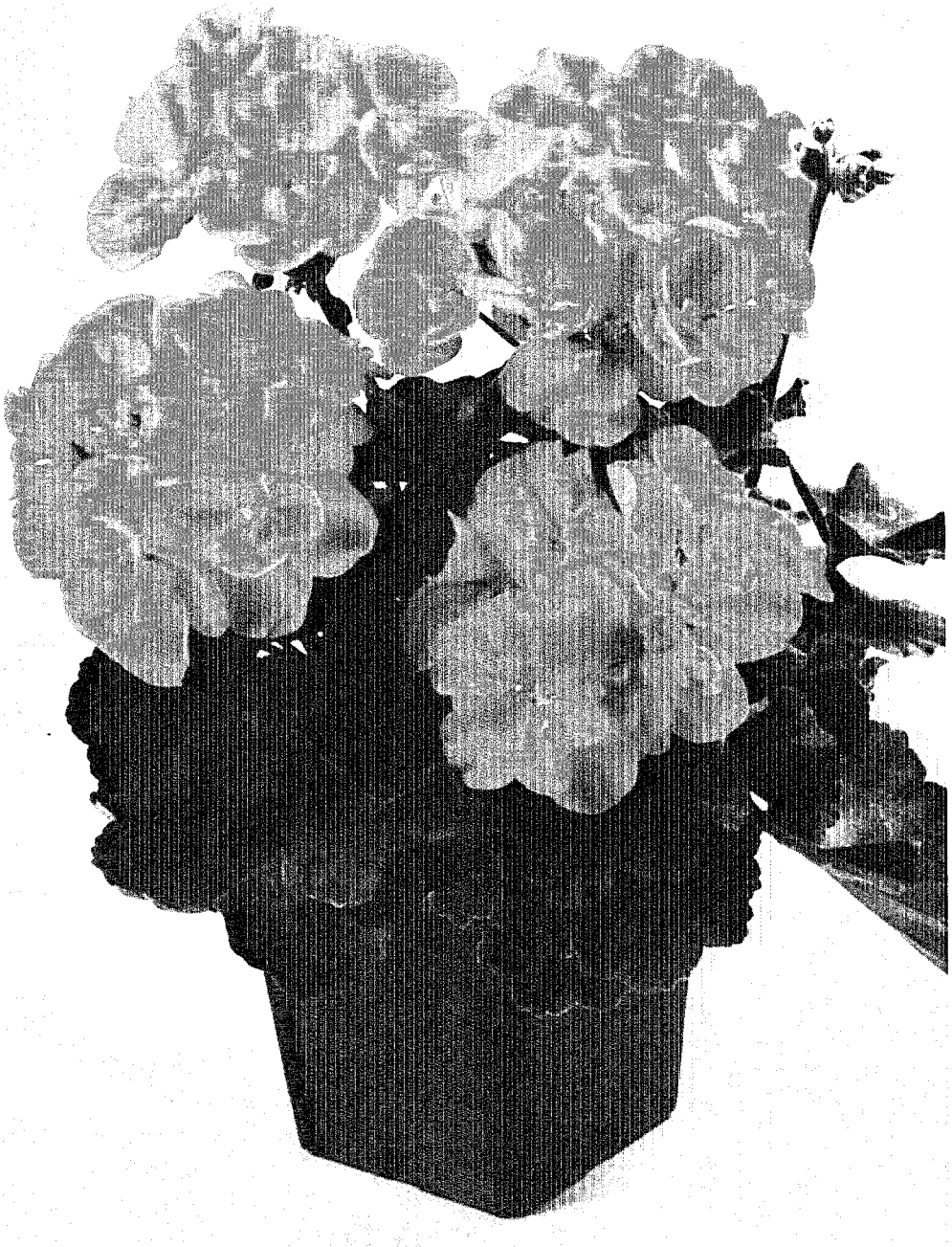

* * * * *